US005494831A

United States Patent [19]
Kindler

[11] Patent Number: 5,494,831
[45] Date of Patent: Feb. 27, 1996

[54] ELECTROCHEMICAL IMMUNOSENSOR SYSTEM AND METHODS

[75] Inventor: Andrew Kindler, San Marino, Calif.

[73] Assignee: Hughes Aircraft Company, Los Angeles, Calif.

[21] Appl. No.: 112,926

[22] Filed: Aug. 30, 1993

[51] Int. Cl.⁶ .................................................. G01N 33/553
[52] U.S. Cl. .................. 436/525; 204/193; 204/400; 204/403; 204/407; 204/411; 204/416; 204/422; 422/82.01; 422/82.02; 422/82.03; 435/817; 435/287.2; 436/518; 436/806
[58] Field of Search .................. 435/7.1, 6, 817, 435/291; 436/501, 525, 518, 806; 422/69, 82.01, 82.02, 82.03; 204/193, 400, 403, 407, 411, 416, 422

[56] References Cited

U.S. PATENT DOCUMENTS

| | | | |
|---|---|---|---|
| 4,072,576 | 2/1978 | Arwin et al. | 436/806 |
| 4,592,894 | 6/1986 | Panitz | 422/69 |
| 4,631,116 | 12/1986 | Ludwig | 204/434 |
| 4,725,140 | 2/1988 | Musha | 356/336 |
| 4,763,413 | 8/1988 | Namba et al. | 356/339 |
| 4,778,769 | 10/1888 | Forrest et al. | 436/501 |
| 4,945,045 | 7/1990 | Forrest et al. | 435/25 |
| 5,074,977 | 12/1991 | Cheung et al. | 204/153.1 |
| 5,082,627 | 1/1992 | Stanbro | 422/82.01 |
| 5,137,827 | 8/1992 | Mroczkowski et al. | 435/288 |
| 5,147,781 | 9/1992 | Rishpon et al. | 435/7.4 |
| 5,149,630 | 9/1992 | Forrest et al. | 435/7.9 |
| 5,156,810 | 10/1992 | Ribi | 422/82.01 |
| 5,234,566 | 8/1993 | Osman et al. | 436/806 |
| 5,298,132 | 3/1994 | Reddy et al. | 204/153.1 |

FOREIGN PATENT DOCUMENTS

| | | |
|---|---|---|
| 4216960 | 11/1993 | Germany . |
| 2276724 | 10/1994 | United Kingdom . |
| WO89/05977 | 6/1989 | WIPO . |
| WO89/11649 | 11/1989 | WIPO . |

OTHER PUBLICATIONS

Journal of Membrane Science, vol. 4, No. 2, Dec. 1978, pp. 221–228, M. Aizawa et al, "Enzyme immunosensor. II. Electrochemical determination of IgG with an antibody–bound membrane".

Journal of Electroanalytical Chemistry and Interfacial Electrochemistry, vol. 258, 1989, pp. 27–39, I. Rosen and J. Rishpon, "Alkaline phosphatase as a label for a heterogeneous immunoelectrochemical sensor. An electrochemical study".

Primary Examiner—David Saunders
Assistant Examiner—Christopher L. Chin
Attorney, Agent, or Firm—M. E. Lachman; M. W. Sales; W. K. Denson-Low

[57] ABSTRACT

A electrochemical immunosensor system is provided which uses electrical signals to measure binding events. The system includes an immunosensor having a sensing electrode in contact with a fluid containing an analyte concentration. A quantity of antibodies or other binding agent is adsorbed on or otherwise affixed to the electrode surface such that a portion of the antibodies of the binding agent binds a portion of the analyte to form complexes on the electrode surface. Signal generating means develop an electrical signal at the sensing electrode such that a response current is produced through the sensing electrode. The response current has measurable signal characteristics which are dependent upon the number of complexes formed, and therefore the analyte concentration within the fluid.

12 Claims, 2 Drawing Sheets

ELECTROCHEMICAL IMMUNOSENSOR SYSTEM AND METHODS

BACKGROUND OF THE INVENTION

1. Field of the Invention

The present invention relates generally to immunologic measurement systems, in which antibody binding is used to measure substance concentration levels. More particularly, the present invention relates to an electrochemical immunosensor in which voltametric signals are used to convert immunosensor binding events to a measurable electrical quantity.

2. Description of Related Art

Immunosensors are a subset of the class of biological measurement instruments commonly known as biosensors. Biosensors typically consist of probes containing biological recognition molecules. The recognition molecules respond to the presence of certain substances, and the response is then converted to a measurable quantity. Biosensors thus provide an indication of substance concentration without the use of complicated laboratory procedures. An immunosensor is a particular type of biosensor in which an antibody serves as the biological recognition molecule. Antibodies are produced in the human body to inactivate foreign substances by irreversibly combining with or binding the substance to form a complex. An almost unlimited variety of antibodies are produced, each specific to a particular substance. The term "antigen" as used herein refers to any substance that can cause the immune system to form antibodies. The term "analyte" will be used to refer to any substance, including an antigen, which binds with any other substance to form a complex. Substances which bind analytes will be referred to as "binding agents". An antibody is one particular type of binding agent. Other binding agents include receptors and affinity-binding molecules.

The highly sensitive and selective nature of antibody binding permits the immunosensor to accurately detect minute analyte concentration levels. Immunsensors are therefore useful in medical applications involving the detection of hormones, illegal drugs or other trace constituents present in blood and urine. Furthermore, since antibodies can be selected to bind to a wide variety of different analytes, the immunosensor has the potential for widespread application to many non-medical uses such as industrial and food processing quality control, monitoring of environmental pollutants and detection of materials used in chemical and biological warfare.

Despite these advantages and potentially widespread applications, immunosensors are not commercially available at the present time. A significant obstacle has been the problem of accurately converting the antibody recognition event to a measurable signal. As a result, more complex measurement techniques are currently used in place of immunosensors. One such group of techniques involves multi-step analytic laboratory procedures known as immunoassays. Several exemplary immunoassays are described in E. Harlow and D. Lane, Antibodies: a Laboratory Manual, pp. 553–612. In applications requiring a highly accurate measurement, the immunoassay techniques used typically require highly trained technicians and costly special equipment. The radioimmunoassay ("RIA") is a good example of this type of highly accurate immunoassay. Measurements are therefore typically performed at a fully equipped central laboratory rather than at remote user locations such as a medical office or a factory. The complex conversion process results in a significant delay before availability of measurement results.

In applications in which a lower degree of accuracy is acceptable, immunoassay techniques which make use of subjective visual examination are typically used. Such techniques provide a convenient but less accurate screen in variety of situations. The subjective tests are often of the "dipstick" type. A sensitized material is placed in the analyte, and a color change on the surface of the material occurs. The pregnancy tests available in most supermarkets are usually of this type. This type of test generally belongs to a class of immunoassays known as enzyme linked immunosorbent assay ("ELISA"). Although ELISA techniques can provide fast results, they are intrinsically less accurate than radioimmunoassay techniques.

There are additional problems with particular immunoassay techniques. For example, one of the most sensitive of the immunoassays is the two-step sandwich type immunoradiometric assay ("IRMA") in which the complexation of an antibody with an antigen is detected by measuring the amount of radioactivity emitted by a radiolabeled antibody. The use of radioactive labels contributes to sensitivity, but exposes laboratory personnel to a significant safety hazard. Moreover, radioactive compounds have a limited shelf life. Other immunoassay techniques, such as fluorescence polarization immunoassay ("FPIA") and ELISA, are safer for laboratory personnel and more stable with regard to shelf life, but are generally less sensitive than the IRMA.

Another alternative to electrochemical immunosensors uses light scattering to convert the antibody binding response to a measurable electrical signal. One such technique uses a spectrometer to measure the variation in the spectrum of laser light passing through a solution containing antibodies and antigens. The antibody-antigen binding response alters the spectral characteristics of the laser in accordance with the antigen concentration level. U.S. Pat. No. 4,725,149 is a variation on this general technique in which laser light is passed through a solution containing antigens and magnetic particles coated with antibodies. The magnetic particles are rotated at a particular frequency by signals applied to coils surrounding the solution such that antibody-antigen binding events produce a measurable variation in the scattered light. In U.S. Pat. No. 4,762,413 a photodetector measures the power spectral density of fluctuations in scattered light intensity, and a mean power spectral density value taken over several measurements is used to indicate antigen concentration.

Light scattering conversion techniques such as these, however, typically utilize expensive specially designed equipment which would tend to limit use at remote sites. In addition, the techniques generally require combining the measurement sample with a buffer solution containing a quantity of particles. The antibodies which will bind to the antigens in the sample are fixed to the surfaces of the particles. Thus, the light scattering techniques are not readily adaptable to those situations in which a sample cannot be easily removed and combined with the particle solution. Furthermore, since the recognition molecules are placed within the particle solution rather than on a probe, the light scattering techniques do not share the advantages of convenience and simplicity commonly associated with biosensors.

Attempts have been made to simplify optical immunosensor detection systems such as those discussed above by attaching antibodies or other binding agents to a deformable organic polymer film. The polymer film absorbs green light and fluoresces strongly in the orange part of the spectrum. When an antibody attached to a surface of the film combines with an analyte, the polymer film is perturbed, causing a detectable decrease in the fluorescence of the film at the point of the combination. The decrease in fluorescence is proportional to the number of analyte molecules bound to antibodies on the surface of the film. The amount of light reflected from the film is measured to determine the analyte concentration in a particular sample. See "Signal Transduction on Film" in Bioventure View, March 1992. Although the polymer film approach may decrease the complexity of the optical immunosensor, it presents additional problems. One such problem is the inability to place a sufficient quantity of binding agents at particular points on the film.

As is apparent from the above, there presently is a need for a simple and inexpensive immunosensor system in which antibody recognition events are rapidly and accurately converted to readily monitored electrical signals using standard electronic test equipment. The immunosensor system should provide highly sensitive, selective and repeatable measurements without the problems associated with immunoassay or light scattering techniques. Furthermore, the immunosensor and related equipment should be easily adapted to the specific requirements of a variety of different uses, including but not limited to medical, industrial, environmental and military applications.

SUMMARY OF THE INVENTION

The present invention uses voltametric electrochemical analysis techniques to accurately convert immunosensor binding events to easily measured quantities. In the electrochemical immunosensor system of the present invention, at least one sensing electrode is provided in contact with a fluid containing an analyte concentration to be measured. The sensing electrode has a surface on which a quantity of a binding agent is present. A portion of the binding agent binds a portion of the analyte within the fluid to form a number of complexes. Signal generating means develop an electrical signal at the electrode, producing a response current signal which is monitored by signal monitoring means. The response current has at least one signal characteristic dependent upon the number of complexes formed, and is therefore indicative of the analyte concentration level within the fluid.

In accordance with one aspect of the present invention, a method for measuring analyte concentrations is provided in which ac voltametric signal is applied to the equipment connected to the immunosensor electrode in order to generate an appropriate response current. Signal characteristics of the response current second harmonic provide an accurate indication of analyte concentration.

In accordance with another aspect of the present invention, a method is provided in which the fluid contains a quantity of indicator ions and wherein an electrical signal is applied to the electrode to generate an ionic response current. The magnitude of the response current varies as a function of the number of antibodies on the electrode surface which have bound analytes in the fluid, which is in turn a function of the analyte concentration.

As a feature of the present invention, the electrochemical immunosensor uses voltametric measurement techniques and readily available test equipment to accurately convert immunosensor antibody binding responses to measurable electrical signals.

As an additional feature of the present invention, the high sensitivity and selectivity of an immunosensor is achieved without the cost and complexity of the present immunoassay or light scattering conversion techniques. The sensor or electrode portion of the electrochemical immunosensor of the present invention can be inexpensively manufactured and therefore discarded after each use. A disposable immunosensor avoids the problems and additional cost associated with cleaning and resurfacing a used sensor.

As a further feature of the present invention, the techniques disclosed can produce inexpensive yet accurate results in many different applications using the same standard set of test equipment and measurement techniques. The electrochemical immunosensor of the present invention therefore permits widespread commercial immunosensor use, resulting in significant benefit to users in many fields. For example, the simple conversion techniques of the present invention will permit remote medical clinics to perform rapid and inexpensive analysis of a variety of constituents, including blood, urine and saliva.

The above-discussed features and attendant advantages of the present invention will become better understood by reference to the following detailed description of the preferred embodiment and the accompanying drawings.

DETAILED DESCRIPTION OF THE PREFERRED EMBODIMENT

The present invention provides a simple and efficient means of converting immunosensor binding events to readily measurable quantities using voltametric electrochemical analysis techniques. One such voltametric technique, disclosed in U.S. Pat. No. 4,631,116, and assigned to the present assignee, uses voltametric signals to produce ac current spectra which vary as a result of changes in the concentration of plating bath trace constituents. The contents of U.S. Pat. No. 4,631,116 are hereby expressly incorporated by reference. Although the following detailed description is primarily directed to using the present invention in conjunction with antibody-antigen binding and exemplary ac voltametric techniques, this is by way of example and not limitation. It should be understood that the system and methods described can be used to detect the concentration of any analyte which binds with any binding agent to form a complex. Many other ac and dc electrical signals or voltametric analytic techniques could also be used to detect binding events in accordance with the present invention.

Figure 1:
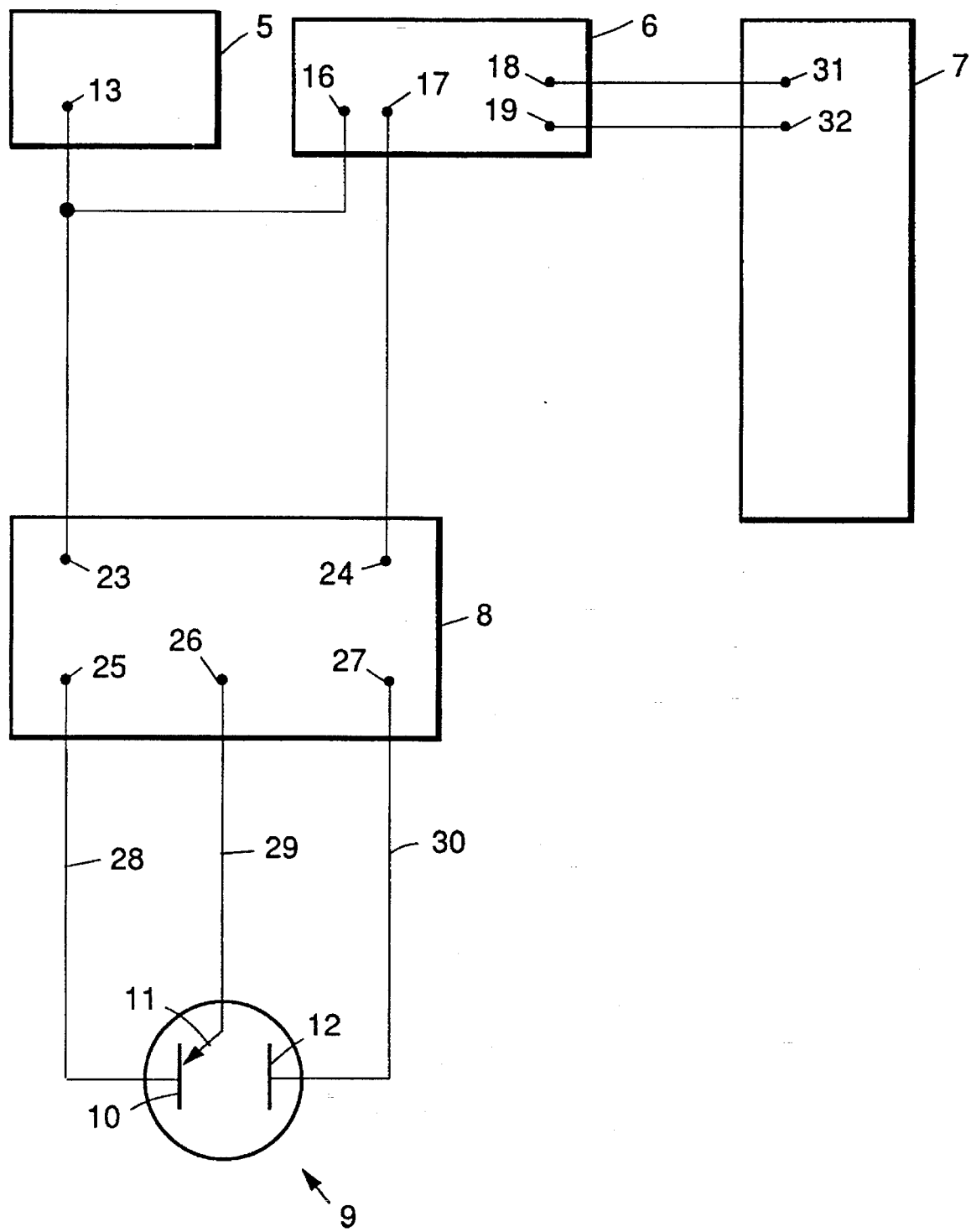
FIG. 1 is a schematic representation of an exemplary preferred embodiment of the electrochemical immunosensor system of the present invention.

The schematic diagram of FIG. 1 shows an exemplary preferred embodiment of the electrochemical immunosensor system of the present invention. The fluid to be measured is located within a sensor 9. The sensor 9 can be submerged within a fluid container or a sample of the fluid may be placed within the sensor. In the case of measurements of bodily fluids, the sensor could be inserted into the body or fluid samples could be removed from the body and placed within the sensor 9 in diluted or undiluted form.

The sensor 9 contains a sensing electrode 10 which is preferably constructed of an inert material such as gold or platinum. Gold is preferred in many applications since it is both inert and known to adsorb antibodies and other proteins very efficiently. A sufficient quantity of antibodies can thus be adsorbed and retained to prevent significant loss of antibodies back to the fluid during voltage excursions into the desorption range of the voltametric signal potential. Platinum has less ability to adsorb antibodies but may be preferred to gold in those applications which do not require as high a rate of antibody adsorption at the electrode. Other inert materials capable of adsorbing antibodies or other binding agents could also be used.

The sensing electrode 10 is connected to port 25 of a potentiostat 8 via line 28. The sensor 9 also contains a counter electrode 12 and a reference electrode 11. All system measurements are taken relative to the reference electrode 11. The reference electrode can be a standard calomel electrode or any other suitable reference electrode. Reference electrode 11 and counter electrode 12 are connected to ports 26, 27 of potentiostat 8 via lines 29, 30, respectively. The three-electrode sensor 9 with electrodes 10, 11 and 12 is a sensor design typically used in conjunction with voltametric techniques. It should be understood, however, that alternative electrode arrangements may also be used with the method of the present invention.

The basic operation of the equipment of FIG. 1 will now be described. A function or waveform generator 5 provides an output 13 which is an ac electrical signal of appropriate waveform, frequency and amplitude. The ac signal is applied to the external input 23 of potentiostat 8 and to the reference input 16 of a lock-in amplifier 6. The ac signal applied to external input 23 of potentiostat 8 may be superimposed upon an appropriate dc voltage sweep signal generated by a sweep signal generator (not shown) housed within the potentiostat enclosure. The sweep signal generator is a separate device but is contained within the housing enclosure of potentiostat 8 for convenience. Alternatively, an external sweep signal generator located outside the potentiostat enclosure could be used to provide the dc sweep signal. The ac signal superimposed on the dc sweep signal is one type of exemplary ac voltametric signal. The ac signal alone is another type of exemplary voltametric signal. When the exemplary voltametric signal is applied to potentiostat 8, a signal substantially equivalent to the applied voltametric signal develops between sensing electrode 10 and reference electrode 11. Potentiostat 8 insures that the developed signal voltage is maintained at the correct value by appropriate application of current to sensor 9.

In the electrochemical immunosensor of the present invention the antibodies or other binding agents are preferably applied to the electrode surface in advance, before the electrode comes into contact with the fluid to be measured. The antibodies may be applied to the electrode surface during the sensor manufacturing process by adsorption or any other suitable technique. Non-electrochemical electrode pretreatment techniques may be used to remove contaminants and otherwise condition the electrode surface for adsorption or attachment of antibodies. Although the electrode material will generally adsorb antibodies without the application of an adsorption signal or potential to the electrode, an adsorption signal may be applied to speed up the adsorption process. An electrochemical conditioning signal may be used prior to measurement to stabilize an electrode which already has antibodies adsorbed or otherwise attached to its surface. Potentiostat 8 or waveform generator 5 can serve to generate an appropriate electrode conditioning signal. The conditioning signal voltage should be carefully monitored to avoid removing or destroying previously attached antibodies.

As discussed above, a signal substantially equivalent to the exemplary voltametric signal applied to the potentiostat 8 is developed between sensing electrode 10 and reference electrode 11 within sensor 9 by application of a current to electrodes 10 and 12. The current is supplied by ports 25 and 27 of the potentiostat via lines 28 and 30 respectively. The current responsible for generating the developed signal has signal characteristics which vary depending upon the electrochemical processes occurring at the surface of the sending electrode 10. This current will be referred to herein as the response current. It is the current generated in response to the applied voltametric signal. Since the electrochemical processes at the sensing electrode surface are a function of antibody-antigen binding, the response current is indicative of antigen concentration in a manner to be further discussed below.

The response current passes back through potentiostat 8, from the potentiostat output 24 to the signal input 17 of lock-in amplifier 6. The lock-in amplifier 6 separates out a desired ac harmonic from the combined ac and dc components of the response current signal and resolves the ac harmonic into an in-phase and a quadrature component. Although either the first or second ac signal harmonic will be most commonly monitored, other harmonics may provide better spectral resolution in a particular application.

The in-phase component of the ac portion of the response current is then passed from in-phase output 18 of lock-in amplifier 6 to a display signal input 31 of strip chart recorder 7. Similarly, the quadrature component is passed from quadrature output 19 of lock-in amplifier 6 to a second display signal input 32 of strip chart recorder 7. The strip chart recorder displays the in-phase and the quadrature components of the selected harmonic of the ac response current as a function of the dc sweep portion of the response current. The quadrature component will include signal peaks indicative of changes in the electrode double layer capacitance. The reference signal supplied from the waveform generator 5 to input 16 of lock-in amplifier 6 is related to the response current signal and permits lock-in amplifier 6 to make accurate relative measurements. Alternative signal monitoring means include digital data acquisition systems, oscilloscopes or any other equipment suitable for displaying or measuring the response current signal. The response current displays represent unique spectral which indicate the analyte concentration in the fluid within sensor 9.

The particular equipment used in the exemplary system of FIG. 1 included a Wavetek Model 188 waveform generator, a PAR 273 potentiostat, and a PAR 5208 lock-in amplifier. The Wavetek waveform generator is available from Wavetek, San Diego, Calif. and the PAR equipment is available from Princeton Applied Research, Princeton, N.J.

The following exemplary methods apply the above described electrochemical immunosensor system to the measurement of antibody binding events. In general, a quantity of antibodies are present on the surface of sensing electrode 10. Although, monoclonal antibodies are preferred, polyclonal or other types of antibodies could be used. A portion of the antibodies on the electrode surface bind a portion of the antigens in the fluid to form complexes on the electrode surface. It should again be emphasized that the use of antibodies in this description is exemplary only, and that other binding agents may be used in place of antibodies.

The entire sensor 9 or individual electrodes therein may be disposable. A disposable sensor or electrode is desirable because the strength of antibody-antigen binding typically makes it difficult to separate antigens from the antibodies on the electrode surface after they have combined to form a complex. A disposable sensor or electrode thus avoids the problems and additional cost associated with cleaning and resurfacing a used sensor. The sensor or electrode can be inexpensively manufactured and supplied in user-ready form. The sensor or electrode can then simply be detached from the remainder of the equipment shown in FIG. 1 and discarded after each measurement.

The first method of converting a binding event to a measurable electrical quantity is based upon the detection of changes in the electrochemical double layer capacitance at the sensing electrode 10. This method involves the application of a voltametric signal consisting of an ac signal superimposed on a dc sweep signal to potentiostat 8. The signal voltage developed at sensing electrode 10 mimics that of the voltametric signal applied to the potentiostat 8. The developed signal is therefore also an ac signal superimposed on a dc sweep. The dc sweep varies linearly over a potential range at a suitable sweep rate.

The antibodies on the electrode surface will bind the corresponding antigen in the fluid irreversibly and with great specificity. At a certain sweep voltage, there will be a tendency for antibodies on the sensing electrode surface to desorb. The complex which is formed as a result of the antibody-antigen binding event will tend to have a different net charge than the antibody alone due to the charge of the antigen. This is particularly true of most proteins, including hormones. Even if the antigen itself is neutral, a charge redistribution within the complex may occur. These charge variations will shift the voltage at which the complex will adsorb and desorb at the electrode relative to an unbound antibody.

At the transition point between absorption and desorption for a particular type of antibody-antigen complex, the ac signal superimposed on the dc sweep will cause the combined ac and dc voltametric signal voltage to oscillate about the average voltage required for transition between the absorbed and desorbed states. The oscillation between the adsorbed and desorbed states causes changes in the response current which can be monitored via lock-in amplifier 6 and strip chart recorder 7 as previously described. The second harmonic of the quadrature current is proportional to the antigen concentration within the fluid. The magnitude or peak of this response current oscillation is proportional to the antigen concentration within the fluid. The second harmonic measurement is preferably monitored because the constant double layer capacitance portion of the response current is thereby effectively filtered out, while the portion of the response current reflecting changes in double layer capacitance is displayed on recorder 7. Very small changes in double layer capacitance can be detected, corresponding to trace levels of antibody-antigen complexes.

The sensitivity of sensing electrode double layer capacitance permits measurement of the antigen concentrations as low as $10^{-12}$ moles/liter. For example, the method can be used to detect certain blood and urine components such as hormones, typically found in concentrations of about $10^{-6}$ to $10^{-12}$ moles/liter, and illegal drug residues, at about $10^{-8}$ to $10^{-9}$ moles/liter.

The high measurement sensitivity of the present invention is a result of a number of factors. One is the fact that the antibodies at the electrode bind so strongly to the analyte that they tend to concentrate the analyte at the electrode. Therefore, even though the bulk concentration of the analyte in the fluid being measured may be low, the analyte concentration at the electrode surface will be relatively high, thereby permitting detection by voltametry. The irreversibility of antibody-antigen binding reduces the minimum detectable analyte concentration significantly below that required in other voltametric measurement applications, such as measuring trace organic in a plating bath analysis system. Another factor contributing to the high sensitivity is the second harmonic filtering effect described above.

The sensitivity of the double layer capacitance to changes in analyte concentration can be increased by adding another species to the fluid containing the analyte. The added species is preferably one which adsorbs at the electrode surface when the complexed analyte desorbs, and vice versa. In this way, the double layer capacitance is affected not only by desorption of the complex, but also by its replacement with the new species. The added species may have a charge if the antibody-analyte complex is essentially neutral. If the complex is highly charged, the added species may either be neutral or have a charge opposite to that of the complex. This will tend to increase the change in the double layer capacitance during desorption of the complex and adsorption of the added species as well as during adsorption of the complex and desorption of the added species.

An exemplary suitable additional species is a surfactant. A surfactant has the desirable property of adsorbing at interfaces such as that provided by an electrode. The adsorption of a surfactant is also less dependent upon charge than the adsorption of other substances. Surfactants with no charge or with either positive or negative charge can easily adsorb. The advantage of using a surfactant is that the choice of charge or lack of charge can be made without regard to whether the species will adsorb. Surfactants of many different types are commercially available, and specialized surfactants can be synthesized. Other species capable of adsorption could also be used, including but not limited to proteins and salts. The choice of material for the added species will typically depend upon the characteristics of the analyte being measured.

In a plot of response current magnitude versus dc sweep voltage, the response current peak due to adsorption of antibody-antigen complexes will appear at a different voltage than the peak due to the adsorption of uncomplexed antibodies alone. As discussed above, the magnitude of the current peak corresponding to the antibody-antigen complex adsorption is indicative of antigen concentration level. However, as the peak representing the complex grows in magnitude, the peak representing the pure antibody will typically get smaller in magnitude. It therefore may be useful in certain applications to monitor the reduction in antibody peak height instead of or in addition to monitoring the complex peak height. For example, the dc sweep voltage at which the complex peak is observable might also be the voltage at which an undesirable electrochemical reaction occurs at the electrode. This reaction may destroy the antibody-antigen complex or cause additives or impurities in the fluid being measured to interfere with the processes occurring at the electrode surface. One such additive may be the surfactant added to the fluid to enhance the magnitude of the changes in double layer capacitance as discussed above. With certain types of additives it may thus become necessary to measure reduction in a pure antibody response current peak instead of or in addition to the antibody-antigen complex response current peak. The use of both peaks also provides a reliability check. For example, a reduction in the pure antibody peak without a corresponding appearance of or increase in a complex peak may indicate an interference with the normal electrode process.

Although the above description is directed to detection of changes in the double layer capacitance following adsorption and desorption of complexes, other types of reactions may also produce detectable changes in the double layer capacitance. For example, certain analytes may be subject to oxidation and reduction during ac voltametry. Once such an analyte is complexed, the oxidation and reduction process can also affect the double layer capacitance. It is therefore possible to use double layer capacitance measurements to detect other reactions such as oxidation and reduction in order to measure concentration of certain analytes.

In order to optimize the accuracy of the response current spectra produced in accordance with the preferred ac voltametric technique described above, a number of independent physical test parameters may be varied. These parameters include, but are not limited to, ac signal amplitude and frequency, dc sweep signal voltage range and sweep range rate, and ac response signal harmonic measured. These parameters should be varied independently to determine the optimal parameter for use in a particular application. In general, certain settings of the above physical test parameters are particularly well-suited for monitoring analyte concentration in accordance with the preferred embodiment of FIG. 1 and the exemplary method described above. The preferred ac waveform is a sinusoid with an appropriate amplitude and a frequency of about 10 to 1000 Hz. The amplitude chosen will depend upon the chemical makeup of the fluid being tested. An appropriate ac signal amplitude should provide measurable changes in the response current while avoiding undesirable reactions between the electrode and the fluid constituents. The preferred frequency range is designed to maximize the quadrature component of the response current for typical applications. Maximizing the quadrature current will maximize the sensitivity to changes in the electrode double layer capacitance. At very high ac signal frequencies, the electrode double layer capacitance will effectively become a short circuit and thereby cause the quadrature component of the current to go to zero. At very low ac signal frequencies, the capacitance behaves like an open circuit, also reducing the quadrature component of the response current to zero. It should be understood that in certain applications ac signal frequencies outside the above preferred range may be desirable. The dc sweep signal is preferably swept over an amplitude range which encompasses adsorption and desorption voltages for the antibodies and antibody-antigen complexes. A preferred sweep rate will typically be an order of magnitude below the ac signal frequency. As previously described, optimal spectral peak resolution is usually obtained using the quadrature component of the ac response current second harmonic.

An alternative method for use with the electrochemical immunosensor system of the present invention detects a binding event by measuring its effect on the impedance at the sensing electrode 10. This method is based upon the formation of an ion gate at the electrode surface. An ion gate is a channel for migration and diffusion of ions from the electrode surface to the fluid under test. The channel can be closed when an antibody on the electrode surface binds an antigen in the fluid. Since the ion gate controls the flow of a relatively large quantity of ions between the fluid and the electrode, a single binding event can produce a measurable change in the response current. The ion gate can therefore be considered the chemical analogue of a transistor. An ion gate is formed by attaching antibodies to gold particles, or other binding agents which are themselves attached to the electrode surface.

In accordance with this alternative method an indicator ion is added to the fluid sample being measured so that an ionic response current will flow through the sensor. The indicator ion need not be capable of reacting electrochemically with the electrode. Any type of ion which does not otherwise unfavorably interact with the system may be used. Preferred indicator ions include chloride salts such as sodium chloride and potassium chloride or other types of salts. Salts are preferred because they tend to maintain a neutral pH and are therefore less likely to affect the pH sensitive proteins used as binding agents or analytes. An ionic response current is then developed when an ac voltametric signal of sufficient frequency is applied to the potentiostat. An ac signal frequency of about 1,000 to 10,000 Hz is suitable for maintaining an ionic response current despite the lack of an electrochemical reaction between the indicator ions and the electrode. The ionic current flow can be maintained via charging and discharging of the electrochemical double layer capacitance at the electrode. The formation of an antibody-antigen complex closes an ion gate and results in a measurable decrease in the ionic response current flow.

Electroactive indicator ions capable of electrodeposition onto the electrode surface may also be used. One exemplary electroactive indicator ion is nickel. In the case of electroactive indicator ions, an ionic response current is developed as a result of the electroactive indicator ions being plated to and stripped from the electrode surface in response to the applied voltametric signal. A binding event can then be readily detected as a decrease in the ionic response current normally associated with plating and stripping of the electroactive indicator ions.

A preferred technique for forming the ion gate is to adsorb antibodies onto colloidal gold particles which include previously adsorbed protein A or G, and then apply the resulting colloidal gold-antibody complex to the surface of the gold electrode using electrophoresis or any other suitable process. A gold electrode is preferred for the reasons discussed above in the general description of the electrochemical immunosensor system. Colloidal gold with adsorbed protein A or G is a commercially available product. The proteins A or G are preferred because they bind to the Fc region or inactive end of an antibody. This allows the active end of the antibody to extend into solution. The colloidal gold-antibody complex will adsorb to the gold electrode, with the antibody acting as a glue between the colloidal gold particle and the gold electrode.

The colloidal gold particles are generally spherical in shape, and as they accumulate on the electrode surface, they will close pack together, leaving small pores between them. The antibodies extend from the surface of the particles into the pore, such that they are exposed to antigens within the fluid. When an antibody binds an antigen, the antigen plugs the pore and thereby closes the ion gate, preventing further passage of ions through the gate. Colloidal gold is available in particle sizes as small as 5 nanometers, and the pores between colloidal gold-antibody complexes will therefore be readily plugged by most antibody-antigen complexes.

The operation of the alternative method is as follows. An electrical signal from waveform generator 5 is applied to potentiostat 8 to which a sensing electrode 10 has been connected as described earlier and as shown in FIG. 1. In this method the ac electrical signal preferably consists of an ac voltametric signal without any dc sweep component. A constant dc potential offset may be added to the ac signal in order to avoid undesirable parasitic reactions. Although it is preferred to keep the dc offset around zero to avoid most parasitic reactions, it may be beneficial to add a positive or negative offset in certain applications. The sensing electrode 10 has a quantity of ion gates formed on it surface by closely packed colloidal gold-antibody complexes adsorbed or otherwise affixed to its surface. A quantity of indicator ions have been added to the fluid containing the analyte to be measured as described above. The ionic response current developed through sensor 9 is then monitored using the lock-in amplifier 6 and strip chart recorder 7 in the manner described previously. The first harmonic of the in-phase component of the ac response current is preferably monitored. In this method, the peak seen on the strip chart recorder 7 will not occur at a particular voltage determined by a sweep signal potential as in the first method described, but instead will occur as soon as the electrode is exposed to the analyte and complexation begins. The magnitude of the ionic response current provides a sensitive indication of analyte concentration.

The accuracy of the response current as an indicator of particular analyte concentrations can be optimized by independently varying system parameters including ac signal amplitude and frequency, constant dc offset and ac harmonic measured. The system parameters preferred for many applications include an ac signal with a frequency of about 1,000 to 10,000 Hz, a dc offset of zero volts, and measurement of the first harmonic of the response current. The ac signal amplitude will again depend upon the binding agent, analyte and other constituents within the fluid under test. The amplitude is chosen such that response current resolution is maximized without causing undesired electrochemical reactions at the electrode. Use of the first harmonic will filter out the constant background current flowing through those ion gates which have not been closed by complexation. The first harmonic can provide this filtering function since the applied voltametric signal no longer includes a dc voltage sweep as in the first method.

Figure 2:
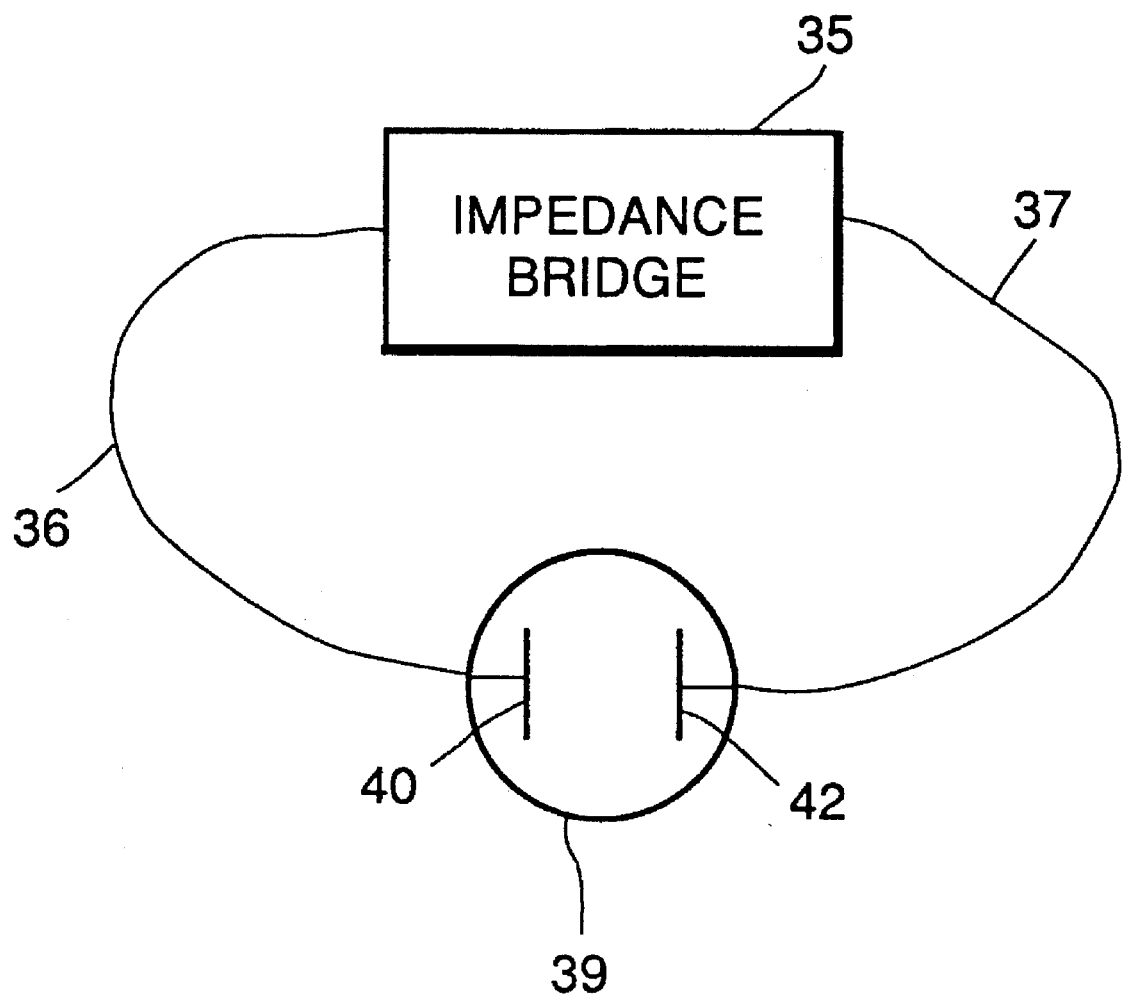
FIG. 2 is a schematic representation of a second preferred embodiment of the electrochemical immunosensor system of the present invention.

FIG. 2 shows an alternative set of measurement equipment for use in conjunction with the above-described ion gate method. The waveform generator 5, lock-in amplifier 6, strip-chart recorder 7 and potentiostat 8 of FIG. 1 can be replaced by the ac impedance bridge 35 of FIG. 2. The ac impedance bridge 35 measures the sensor impedance by applying an ac signal and monitoring the current through the sensor. The ac impedance bridge 35 can thus serve as both a signal generating means and a signal monitoring means.

The impedance bridge 35 generates an ac signal of appropriate amplitude and frequency and applies it via leads 36 and 37 to sensor 39. The sensor 39 includes a sensing electrode 40 and counter electrode 42. When an ac impedance bridge is used as a signal generating and monitoring means a reference electrode need not be included in sensor 39. Sensor 39 contains a quantity of indicator ions and sensing electrode 40 has a quantity of antibodies present on its surface in accordance with the above described ion gate method. The applied ac signal from impedance bridge 35 causes an ionic response current to flow between electrodes 40 and 42. Antibodies complexing with analytes within sensor 39 close ion gates on the sensing electrode surface and thereby increase the impedance and reduce the ionic response current flowing through sensor 39. The increased impedance is monitored by impedance bridge 35 and is proportional to the number of complexes formed at the sensing electrode surface, which is a function of analyte concentration.

Commercially available impedance bridges typically provide an ac signal at about 1,000 Hz. This is within the frequency range discussed above which permits an ionic current resulting from charging and discharging of the electrode double layer capacitance. The indicator ion within sensor 39 therefore need not be electroactive. Although under certain circumstances the 1,000 Hz typically provided by commercially available impedance bridges may be too low a frequency for optimal operation, custom designed impedance bridges could be constructed to provide a desired frequency of operation.

Although the above description has been directed to the use of exemplary voltametric techniques to detect antibody-antigen binding events and thereby antigen concentration levels, this is by way of illustration and not limitation. The electrochemical immunosensor system and methods of the present invention can be applied to detect any analyte which binds with any binding agent to form a complex. Other voltametric techniques and equipment could also be applied to analyte detection using the methods of the present invention. It will be understood by those skilled in the art that many alternate embodiments of this invention are possible without deviating from the scope of the invention, which is limited only by the appended claims.

What is claimed is:

1. An electrochemical immunosensor system adapted for use in measuring a concentration of analytes in a fluid, said system comprising:

an immunosensor having at least one sensing electrode for contact with said fluid, said sensing electrode being constructed of a material selected from the group consisting of gold and platinum and having a surface on which a binding agent consisting of antibodies is present, such that a portion of said binding agent binds a portion of said analyte in said fluid to form a number of complexes;

signal generating means electrically connected to said sensing electrode for generating an electrical signal for application to said sensing electrode comprising:
a waveform generator which provides an ac signal;
a potentiostat having an input to which said ac signal is applied and an output electrically connected to said sensing electrode; and,
a dc signal generator which provides a dc sweep signal, wherein said electrical signal at said sensing electrode includes said ac signal superimposed on said dc signal wherein said electrical signal produces a response current having at least one signal characteristic which is dependent upon said number of complexes; and signal monitoring means electrically connected to said response current for monitoring said signal characteristic of said response current and comprising phase-locking means for tracking potions of said response current that are at a specified phase angle with respect to a reference signal.

2. The immunosensor system of claim 1 wherein said signal generating means and said signal monitoring means include an impedance bridge.

3. The immunosensor system of claim 1 wherein said sensing electrode having said binding agent present on said surface thereof is disposable.

4. The immunosensor system of claim 1 wherein said immunosensor is disposable.

5. A method of measuring an analyte concentration using an immunosensor, said method comprising the steps of;

providing a fluid containing an analyte concentration to be measured;

providing an immunosensor having at least one sensing electrode, said sensing electrode having a surface on which a binding agent consisting of antibodies is present;

placing said sensing electrode of said immunosensor in contact with said fluid such that a portion of said binding agent on said sensing electrode surface binds a portion of said analyte in said fluid to form a number of complexes;

developing an electrical signal at said sensing electrode on which said complexes are formed, said electrical signal comprising a voltametric signal including an ac signal superimposed on a dc sweep signal, said ac signal having an amplitude and a frequency and said electrical signal producing a response current flowing through said sensing electrode having at least one signal characteristic which is dependent upon said number of complexes; and monitoring said signal characteristic of said response current by measuring an ac component of said response current as said dc signal is swept over a potential range, said measurement of said ac component of said response current in relation to said dc potential range being expressed as ac current spectra wherein said analyte concentration is determined from said ac current spectra.

6. The method of claim 5 further including the step of adding an additional species to said fluid containing said analyte, said additional species capable of adsorbing to said electrode at a voltage at which said complex desorbs from said electrode and desorbing from said electrode at a voltage at which said complex adsorbs to said electrode.

7. The method of claim 5 wherein measurement of said ac current is made at the second harmonic frequency relative to the frequency of said ac signal.

8. A method of measuring an analyte concentration using an immunosensor, said method comprising the steps of:

providing a fluid containing an analyte concentration to be measured and a quantity of indicator ions wherein said ions provide for an ionic current;

providing an immunosensor having at least one sensing electrode, said sensing electrode having a surface on which a binding agent consisting of antibodies attached to gold particles is present wherein said binding agent forms a quantity of ion gates on said surface of said sensing electrode;

placing said sensing electrode of said immunosensor in contact with said fluid such that a portion of said binding agent on said sensing electrode surface binds a portion of said analyte in said fluid to form a number of complexes;

developing an electrical signal at said sensing electrode on which said complexes are formed, said electrical signal being produced by an impedance bridge and producing an ionic response current flowing through said sensing electrode having at least one signal characteristic which is dependent upon said number of complexes wherein said complexes close one or more of said ion gates and thereby reduce a magnitude of said ionic response current; and monitoring said signal characteristic of said ionic response current by means of said impedance bridge to determine said analyte concentration.

9. The method of claim 8 wherein said electrical signal comprises an ac signal having an amplitude and a frequency.

10. The method of claim 9 wherein said ac signal has a frequency of about 1,000 to 10,000 Hertz.

11. The method of claim 8 wherein said binding agent which forms said ion gates includes a number of antibodies bound to particles of colloidal gold having adsorbed protein.

12. The method of claim 8 wherein the measurement of said ac current is made at the first harmonic frequency relative to the frequency of said ac signal.

* * * * *